US00PP26652P3

(12) United States Plant Patent
Beeson

(10) Patent No.: US PP26,652 P3
(45) Date of Patent: Apr. 26, 2016

(54) ***PAULOWNIA* TREE NAMED 'NRJNJF13'**

(50) Latin Name: *Paulownia renova*
Varietal Denomination: NRJNJF13

(71) Applicant: Dennis Beeson, Bakersfield, CA (US)

(72) Inventor: Dennis Beeson, Bakersfield, CA (US)

(73) Assignee: Spring Innovations, Bakersfield, CA (US)

( * ) Notice: Subject to any disclaimer, the term of this patent is extended or adjusted under 35 U.S.C. 154(b) by 0 days.

(21) Appl. No.: 13/998,809

(22) Filed: Dec. 9, 2013

(65) Prior Publication Data

US 2015/0163977 P1 Jun. 11, 2015

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Susan McCormick Ewoldt

(74) *Attorney, Agent, or Firm* — R. Scott Kimsey, Esq.; Klein DeNatale Goldner et al.

(57) ABSTRACT

The invention relates to a new and distinct variety of *Paulownia* tree denominated 'NRJNJF13.' The invention is a rapidly-growing variety distinguished from its parent varieties in terms of flower color, time of bloom, seed pod size and shape, and rate of growth.

4 Drawing Sheets

Latin name: *Paulownia renova.*
Varietal denomination: 'NRJNJF13'.

RELATED APPLICATIONS

Not applicable.

BACKGROUND OF THE INVENTION

1. Field of the Invention

The present invention relates to a tree of the genus *Paulownia.*

2. Background

The *Paulownia* genus includes from nine to twelve species, depending on the taxonomic authority consulted. The plants are in the family Paulowniaceae, and are related to, and sometimes included in, the family Scrophulariaceae, commonly known as the Figwort family. The *Paulownia* tree is a deciduous tree native to China and known for its rapid growth, profuse spring bloom of foxglove-like flowers, and large catalpa-like green leaves.

*Paulownia* is important for lumber production, owing largely to its rapid growth. The wood of the tree is also used in the production of chests, boxes, and some musical instruments, as well as any other use for which a fine-grained, soft wood is desirable.

SUMMARY OF THE INVENTION

The present invention relates to a new and distinct variety of *Paulownia* tree. The new cultivar, denominated 'NRJNJF13' parented via the uncontrolled pollination of *Paulownia fortunei* and a rapid-growth genetic hybrid *Paulownia* tree referred to by the inventor as 'Megafolia.' 'Megafolia' is a cross between a *Fortunei* 'Select #2' clone referred to by the inventor as "Baby Huey," and a *Paulownia kawakamii*. Baby Huey was discovered by the inventor as a chance seedling on his *Paulownia* tree farm in Bakersfield, Calif. 'Megafolia' is believed to have been parented from the *Paulownia* tree known as Baby Huey based on its characteristics and close proximity to Baby Huey in the area of discovery. Baby Huey was known by the inventor to be a *Paulownia fortunei* 'Select #2' clone, and was selected by the inventor due to its rapid seed emergence and subsequent remarkable rate of growth.

The 'NRJNJF13' cultivar was selected by the inventor due to its relative vigor and rapid growth as compared to other *Paulownia* seedlings, its early bloom emergence, the relatively small size of its seed pods, and the deep purple color of its flowers. These characteristics serve to readily distinguish 'NRJNJF13' from its parent plants. 'NRJNJF13' has flowers of a deeper purple color than *Paulownia kawakamii*, an approximately four to five week earlier bloom, smaller rounder seed pods, and an approximate 20% increase in growth rate. 'NRJNJF13' is distinguished from *Paulownia fortunei* in having deep purple rather than white lavender blooms, an approximately three week earlier bloom, much smaller rounder seed pods, and an approximate 10% increase in rate of growth.

The propagated trees of 'NRJNJF13' have been determined to be stable, reproducible, and true to type in successive generations, with each generation exhibiting consistently higher growth rates than any other *Paulownia* species known to the inventor. Propagation was accomplished through the use of root cuttings. A cutting of approximately two inches was taken from an existing 'NRJNJF13' tree and the cuttings were grown in a greenhouse in Bakersfield, Calif. at a temperature range of from about 85° F. to about 93° F. Root cuttings were planted in the months of October, November, December, January, and February, and the resulting trees planted when the root cuttings developed leaves and a stalk of about five inches in height.

DETAILED BOTANICAL DESCRIPTION

Figure 1:
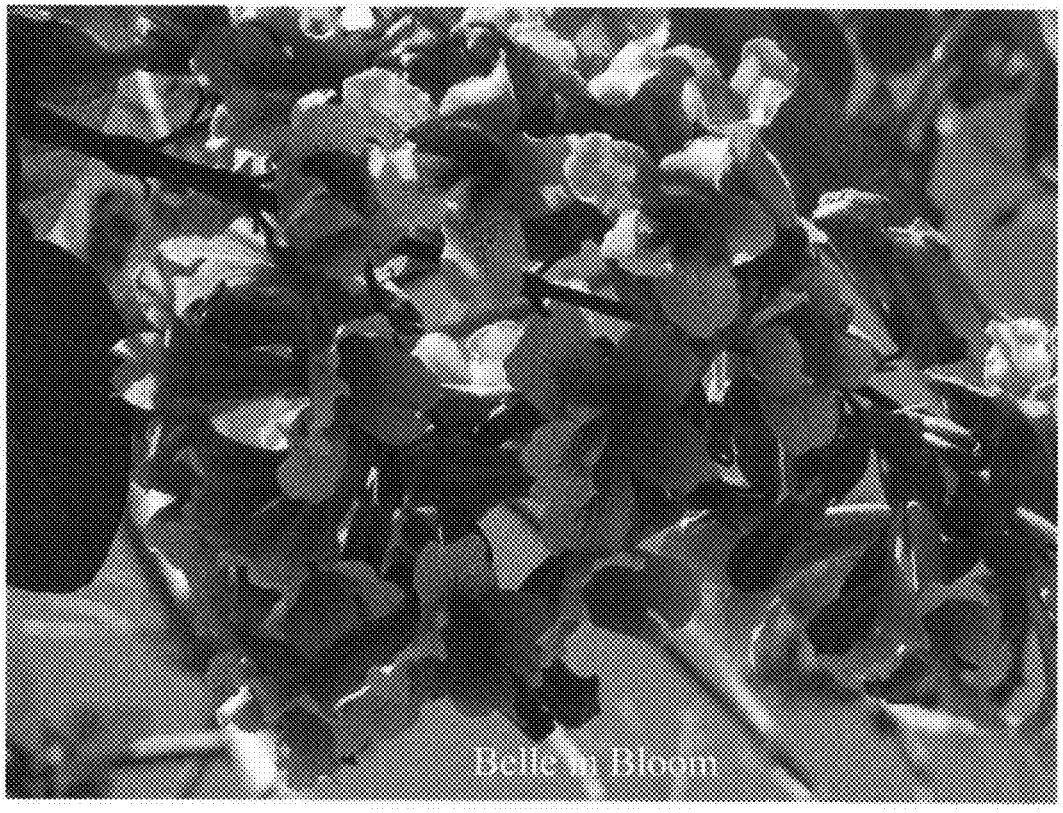
FIG. 1 is a color photograph showing the typical size, shape, and color of the blossoms of the new variety in summer.
Figure 2:
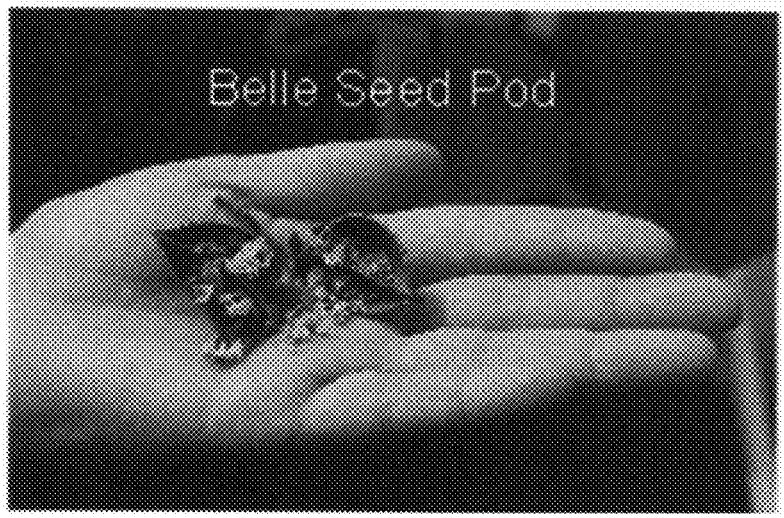
FIG. 2 is a color photograph of the new variety showing the typical size, shape and color of seed pods of the new variety, in contrast to see pods from the variety referred to herein as 'Megafolia.'
Figure 2:
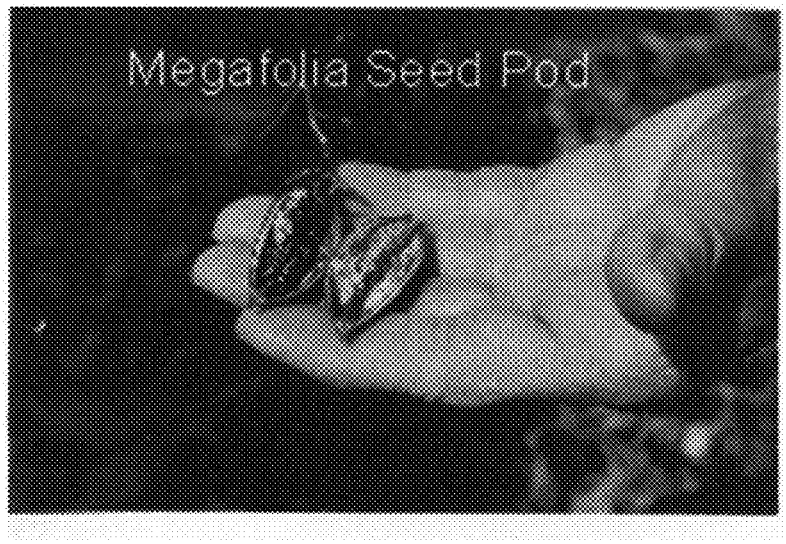
Figure 3:
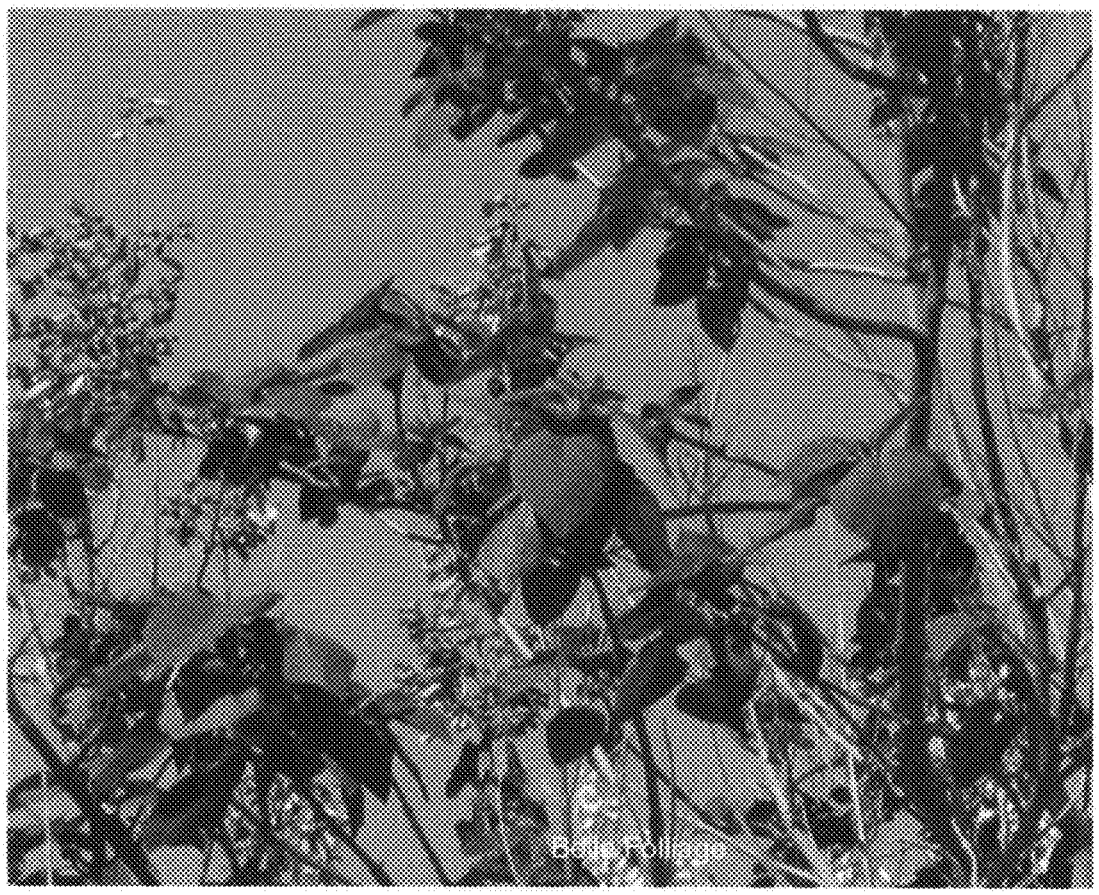
FIG. 3 is a color photograph of the new variety showing the typical coloration of growth found on the inner part of the current variety during summer, with the color ranging from green foliage to leaves with advancing dark green from the leaf petiole and the leaf base down the leaf blade.
Figure 4:
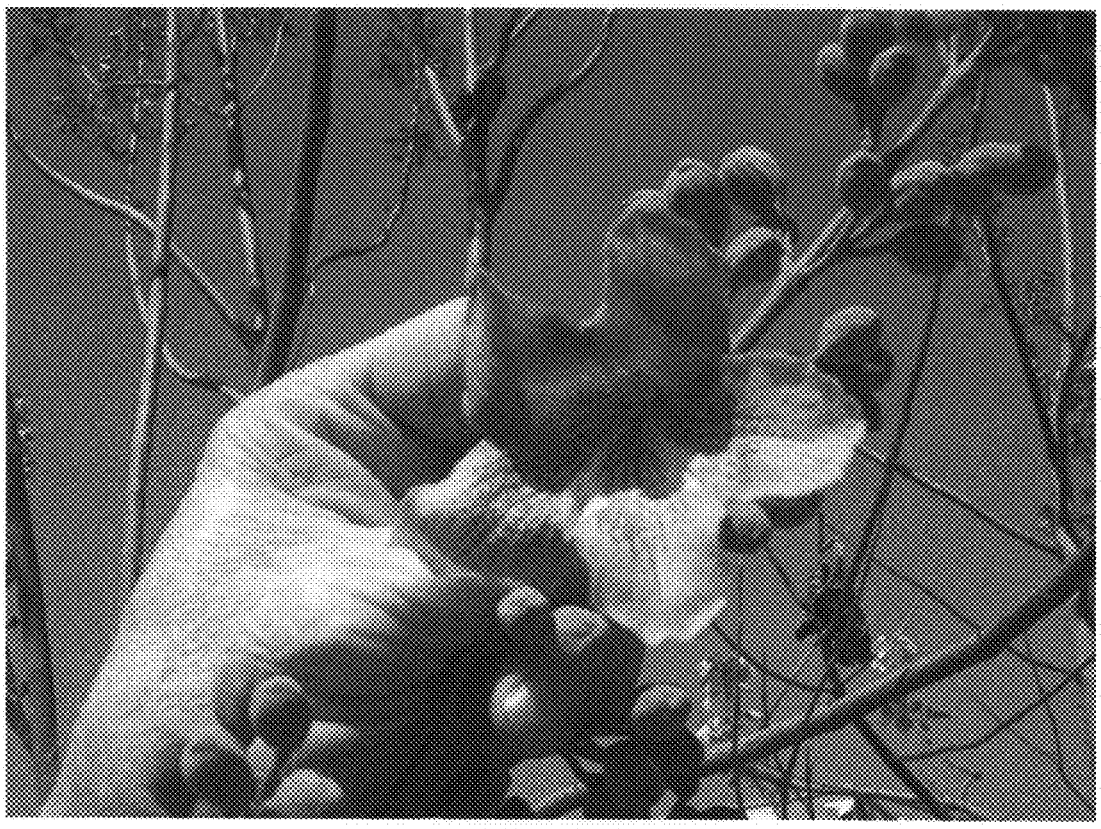
FIG. 4 is a color photograph showing a close view of a flower of the new variety.

The new and distinct variety of *Paulownia* described herein has a number of stable, representative characteristics that have been observed in representative specimens of the variety, grown and observed in Bakersfield, Calif. The 'NRJNJF13' cultivars grown and observed are distinguished from other *Paulownia* varieties by a set of characteristics exhibited by the new variety. 'NRJNJF13' cultivars typically grow to a height of over twenty feet within one year, and are suitable for harvesting for commercial lumber within three years. The new variety also exhibits limbs that are upright to spreading, with a rounded crown. 'NRJNJF13' cultivars have ovate, green leaves, up to 5" to 7" in length, that are lightly hairy above and densely hairy and sticky beneath the leaves. The variety also have a profuse bloom of fragrant, tubular, funnel-shaped purple flowers, up to 2½" in length, with interior dark purple spotting and creamy yellow striping. The flowers appear in spring, in clusters up to 14" long, before the appearance of the foliage. The aroma of the flowers is reminiscent of lilac. The flowers are followed by oval, woody, dehiscent seed capsules that emerge sticky green and ripen to brown in fall, at which point they split open, releasing winged seeds at a number approximately 80% fewer than existing *Paulownia* varieties. 'NRJNJF13' exhibits tree bark that is gray in color and flaky in texture. The sap of the tree is very sweet in flavor and, when measured by the Brix test using a refractometer, is comparable to a pineapple (i.e. from 20+ on the Brix scale).

The following is a botanical description of the characteristics of the new variety as displayed by specimens grown in Bakersfield, Calif. Tree trunks were trimmed to the ground (coppice) in year two of growth. References to color are made in accordance with the colors on The R.H.S. Colour Chart (1995 ed.), published by The Royal Horticultural Society, London, England. Coloration of leaves and bark may be variable due to conditions of nutrition, stress, age of tree, location on tree, and the presence or absence of sun or shade. Tree part comparisons have been made from a mature tree, where growth rates and characteristics are considered typical.

Flowers: Inconspicuous purplish lavender true flowers in sessile in compact umbels are surrounded by a showy white involucre much exceeding the flowers. The true flowers are (Green Group 143C) at petal tip and (Yellow-Green Group 15D) at petal base on the lower surfaces and (Green-White Group 157C) on upper surfaces. The rounded, central umbel is approximately a cm wide by 1 cm high at the top of a peduncle 5 to 6 cm in length and greenish (Yellow-Green Group 144C). The valvate—4 petaled flowers consist of four stamens (Green-White Group 157C) with filament (Green-White Group 157C) of 2 mm length by 0.5 mm wide. The anther, initially translucent and 0.755 mm to 1 mm long by 0.5 cm wide, matures to a brown (Brown Group 200A). One columnar pistil per flower with ovary color (Greyed-Purple Group 187A). The style is of (Greyed-Purple Group 187A) and 1 mm by 0.5 mm wide. The stigma is flat, and greenish-yellow (Yellow-Green Group 150D) at first, maturing to (Greyed-Purple 187A) and 0.5 mm in width. The number of inconspicuous flowers will vary per umbel and do not all open at the same time—opening from outside in. The involucre of four partially overlapping smooth, entire, oval-acuminate creamy white bracts form a four-pointed symmetrical star characterizing each individual inflorescence. Initially, bracts with rounded base and acuminate apices are white (White Group 155C) on upper side and (White Group 157D) underneath. Mature bracts resemble (Green-White Group 157A) above, (Green-White Group 157D), below. Typical and observed bract size averages 4.5 to 5 cm long and 3.5 to 4 cm wide, thereby producing an inflorescence with an overall width of 9 to 10.5 cm. Flowering commences the last week of April to the first week of May, in Bakersfield, Calif., lasting about six weeks. Flowers of this cultivar are borne more on the inside of the tree and are not overly abundant.

Fruits: The fruits connate into a globular, fleshy head, predominantly red (Red Group 46C) and approximately 3 cm in diameter at maturity. The syncarp is initially held upright on a 5 to 6 cm peduncle, later becoming pendulous.

Buds: Buds are two types—Globose, tapering flowe buds averaging 7 mm in length by 5 mm in width at the base, color gray-brown (Gray-Brown Group 199A) and sharply tapered vegetative buds averaging 4 mm in length by 2 mm in width at basae, color brown (Brown Group 200B).

Leaves: Deciduous, simple, entire leaf, elliptic ovate with acuminate tips and cuneate bases, 12.7 to 17.8 cm long and 3.5 to 7.5 cm wide. Leaf petioles are 5 to 10 mm long by 2 mm in diameter on average and of the color (Yellow-Green 144D0. Leaf blades are glabrous on top, glabrous underneath, and lacking tufts of hairs in leaf vein axils on the underside of leaf. Newly emerging leaves in the spring exhibit yellow green (Yellow-Green Group 144B) on the upper side of the leaves and (Yellow-Green Group 144C) underneath, darkening to green (Green Group 139A) on the upper side of leaves and (Green Group 139B) below. Many leaves of the current year's growth flush became yellow (Yellow Group 13B) by midsummer. The yellow coloration is exhibited from leaf petiole and base down leaf blade and may include from ⅓ to entire leaf. Coloration begins in July. Overall, the current season's growth found on the inner part of the tree may range from green foliage to leaves with yellow advancing down the leaves to varying degrees. The more vigorous new growth on the outside canopy exhibits mainly solid yellow leaves. At maturity, yellow leaves develop red blushes (Red Group 46B) with the yellow predominating. Much later, these blushed yellow leaves become infused with more red (Red Group 46B and 46C) and orange (Red Group 42B and 42C) fall colors. Leaves that have remained green will later exhibit red (Red Group 46B and 46C) and orange (Red Group 42B and 42C) fall colors typical of the species. The yellow coloration of the foliage appears year after year regardless of weather conditions. The leaves exhibit trichomes that are approximately 25% less dense than those found in *Paulownia tomentosa*.

Stems: Young stems are initially slender, glabrous grey green (Greyed-Green Group 194C) with whitish (Greyed-White Group 156C) lenticels present on all bark areas diminishing somewhat on more mature surfaces to orange (Orange-White Group 159A). Typical observed lenticel height is 1 mm times 0.5 mm diameter. 45 to 68 lenticels are present per square centimeter. Slightly textured, smooth bark on the lower trunk 15.25 cm from the ground is of the color grey green (Greyed-Green 197A). Trunk diameter is 4 cm at 15.25 cm.

Branches: New shoots are green (Yellow-Green Group 144C) turning to grey orange (Greyed-Orange 177A) over time. One and two year old twigs are grey orange (Greyed-Orange Group 165A). The final 2.5-10 cm of the twig, exclusive of terminal buds, may be flushed red-purple (Red-Purple Group 58A) on the upper side of the branch and green (Green Group 143C) on the lower side. Mature branch color is grey green (Greyed-Green Group 197A).

Form, size and branching characteristics: A shrubby tree six to ten meters in height and spread at maturity. Rounded as a young tree, maintaining that shape with a layered, horizontal branching habit. A wide range of factors, especially age, location, and whether the tree is multi-stem or single stem, influences the size of stems and branches. There is no predictable correlation between the diameter of a primary stem and any branch arising from it. Height and trunk diameter (at ground level), respectively, were measured at 26 feet and 13 inches in year 6; 29 feet and 15 inches in year 7; 33 feet and 17 inches in year 8; and 36 feet and 19 inches in year 9.

Tolerance: The new variety is tolerant to a wide range of temperatures, growing well from climate zones 6 to 10, as designated by the U.S.D.A. plant hardiness zone map. This corresponds to an average minimum temperature range of from about −10° F. to about 40° F., according to U.S.D.A. data from 1976 to 2005. 'NRJNJF13' has been found to thrive over a range of soil conditions and characteristics. The range of soil nutrients and characteristics in which the new variety grows includes: SP 15-55; pH 4.5 to 8.8; Ec 0.2 to 10 mmHo; % Ca 10 to 95; Mg 0.1 to 10 Epm; Na 0.05 to 20 Epm; B 0.01 to 10 ppm; Na 0.05 to 20 Epm; $NO_3$/N 0.01 to 150 ppm; $PO_4$/P 1 to 200 ppm; K 5 to 1000 ppm; Zn 0.01 to 200 ppm; Fe 0.01 to 900 ppm; Mn 0.01 to 900 ppm; Cu 0.01 to 100 ppm; $SO_{4-5}$ 5 to 10,000 ppm; Organic 1 to 10%; Chloride 1 to 25 Epm; Total Dissolved Solids in $H_2O$ 2 to 8 ppm.

Growth rate: Moderate, more rapid in youth.

Pests, diseases: May be susceptible to Powdery Mildew, Borer (Dogwood).

Having thus described the preferred embodiment of the invention, what is claimed as new and desired to be protected by Letters Patent includes the following:

1. A new and distinct variety of *Paulownia* tree as substantially illustrated and described herein.

* * * * *